US009034410B2

(12) United States Patent
Vella et al.

(10) Patent No.: US 9,034,410 B2
(45) Date of Patent: May 19, 2015

(54) WHOLE GREEN COFFEE BEAN PRODUCTS AND METHODS OF PRODUCTION AND USE

(76) Inventors: Thomas J. Vella, Scottsdale, AZ (US); Samuel A. Amen, Cave Creek, AZ (US)

(*) Notice: Subject to any disclaimer, the term of this patent is extended or adjusted under 35 U.S.C. 154(b) by 185 days.

(21) Appl. No.: 13/215,174

(22) Filed: Aug. 22, 2011

(65) Prior Publication Data

US 2011/0305792 A1 Dec. 15, 2011

(51) Int. Cl.
A23F 5/00 (2006.01)
A23F 5/02 (2006.01)
A23F 5/08 (2006.01)
A61K 36/74 (2006.01)

(52) U.S. Cl.
CPC ... *A23F 5/02* (2013.01); *A23F 5/08* (2013.01); *A61K 36/74* (2013.01)

(58) Field of Classification Search
CPC ........ A23L 1/3002; A23L 1/0026; A23L 2/39
USPC .............................. 426/59, 455; 424/464, 451
See application file for complete search history.

(56) References Cited

U.S. PATENT DOCUMENTS

| 5,160,757 | A | 11/1992 | Kirkpatrick et al. |
| 2007/0190207 | A1 | 8/2007 | Takahashi et al. |
| 2009/0053382 | A1* | 2/2009 | Kawamura et al. ........... 426/595 |
| 2009/0175973 | A1 | 7/2009 | Vikhrieva |
| 2009/0232954 | A1 | 9/2009 | Imison |
| 2009/0264524 | A1 | 10/2009 | Sadachi et al. |
| 2010/0112098 | A1 | 5/2010 | Lemaire et al. |
| 2011/0039012 | A1 | 2/2011 | Fields |
| 2011/0126314 | A1 | 5/2011 | McCarthy et al. |
| 2011/0189313 | A1 | 8/2011 | Shimoda et al. |
| 2011/0305792 | A1 | 12/2011 | Vella et al. |

FOREIGN PATENT DOCUMENTS

WO WO 2004098303 A1 * 11/2004 ............... A23F 5/02
WO 2010/124936 A1 11/2010

OTHER PUBLICATIONS

Chu, Yi-Fang, Coffee Emerging Health Effects and Disease Prevention, Wiley-Blackwell, 2012, p. 86.*
Charalambous, George, Handbook of Food and Beverage Stability, Chemical, Biochemical, Microbiological and Nutritional Aspects, Academic Press, Inc. 1986, pp. 686. http://books.google.com/books?id=_a1B1RukgAwC&pg=PA686
&dq=water+content+of+green+coffee+beans+harvested&hl=en
&sa=X&ei=O2C1U6T9DLKqsQT48oHICg
&ved=0CC4Q6AEwADgK#v=onepage&q=water%20content.*

(Continued)

*Primary Examiner* — Michele L Jacobson
*Assistant Examiner* — Hong T Yoo
(74) *Attorney, Agent, or Firm* — Bennett Intellectual Property; Allen F. Bennett

(57) ABSTRACT

Disclosed are novel processing methods for green coffee beans that result in novel green coffee bean products, including products that incorporate whole green coffee beans. Methods include selecting whole coffee beans in their fresh green unroasted state with naturally-occurring levels of phytonutrients, sterilizing and drying them, applying iterative grinding processes and stabilization techniques, all while avoiding high temperatures. Whole green coffee bean products created and defined by these methods have unexpectedly been found to increase focus and concentration in users, and are believed useful in the treatment of attention and concentration deficits and related disorders, such as attention deficit (AD), attention deficit disorder (ADD), attention deficit hyperactivity disorder (ADHD), and various related and/or comorbid disorders.

19 Claims, 6 Drawing Sheets

(56) References Cited

OTHER PUBLICATIONS

United States Federal Emergency Management Agency, Food and Water in an Emergency, 2009, pp. 11.*

Webster-Merriam, definitation of sterilize obtained on Jul. 3, 2014.*

Wikipedia, sterilization obtained on Jul. 3, 2014.*

PCT/US2012/51585 International Search Report and Written Opinion of the ISA (US).

PCT/US2012/51585 Chapter II Demand, Amendment, and Response to Written Opinion of the ISA.

PCT/US2012/51585 Preliminary Report on Patentability.

* cited by examiner

WHOLE GREEN COFFEE BEAN PRODUCTS AND METHODS OF PRODUCTION AND USE

TECHNICAL FIELD

The present invention relates to methods of processing green coffee beans, products obtained and defined by those methods, and methods of treatment using those products.

BACKGROUND

The term "coffee bean" collectively refers to the seeds (coffee seeds) that are obtained by the refining process of removing the pulp and the skin from the berries (known as coffee berries or coffee cherries) of *Coffea* plants, and the beans that are produced from these. Coffee berries, which contain the coffee bean, are produced by several species of small evergreen plants of the genus *Coffea*, which are of the family Rubiaceae. The two most commonly grown species are *Coffea robusta* (also known as *Coffea canephora*) and *Coffea arabica*. These are typically cultivated in Latin America, Southeast Asia, and Africa. "Green" coffee beans are coffee beans that have not yet passed through a roasting process, such as the roasting process used in the production of coffee.

The various steps in the production of coffee are described in Smith, A. W., in Coffee; Volume 1: Chemistry pp 1-41, Clark, R. J. and Macrea, R. eds, Elsevier Applied Science London and New York, 1985; Clarke, R. J., in Coffee: Botany, Biochemistry, and Production of Beans and Beverage, pp 230-250 and pp 375-393; and Clifford, M. N. and Willson, K. C. eds, Croom Helm Ltd, London, as described in U.S. patent application Ser. No. 12/941,557 titled Modulation Of Coffee Flavour Precursor Levels In Green Coffee Grains, filed Nov. 8, 2010 on behalf of McCarthy, et al., and published on May 26, 2011 as publication number U.S. 2011/0126314 A1 (hereafter "McCarthy"), the entirety of which is incorporated herein by reference as though set forth in full herein. The process typically starts with the collection of mature, ripe red coffee cherries. The outer layer, or pericarp, can then be removed using either the dry or wet process. The dry process is the simplest and involves: (1) classification and washing of the cherries; (2) drying the cherries after grading (either air drying or mechanical drying); and (3) dehusking the dried cherries to remove the dried pericarp. The wet process is slightly more complicated, and generally leads to the production of higher quality green beans. The wet process is more often associated with *C. arabica* cherries. The wet process may comprise: (A) classification of the cherries; (B) pulping of the cherries (this step is done soon after harvest and generally involves mechanical removal of the "pulp", or pericarp, of the mature cherries); (C) "fermentation," where the mucilage that remains attached to the grain of the cherries after pulping is removed by allowing the grain plus attached mucilage to be incubated with water in tanks using a batch process. The "fermentation" process is allowed to continue up to 80 hours, although often 24 hours is generally enough to allow an acceptable fermentation and to cause the pH to drop from around 6.8-6.9 to 4.2-4.6, due to various enzymatic activities and the metabolic action of microorganisms which grow during the fermentation. The next steps, (D) drying, involves either air or mechanical hot air drying of the fermented coffee grain, and (E) "hulling," involves the mechanical removal of the "parch" of the dried coffee grain (dried parchment coffee) and often the silverskin. After wet or dry processing, the resulting green coffee grain are often sorted, with most sorting procedures being based on grain size and/or shape.

The next step in the production of conventional coffee is the roasting of the green grain after dehusking or dehulling of dry or wet processed coffee, respectively. This is a time-dependent process which induces significant chemical changes in the bean. The first phase of roasting occurs when the supplied heat drives out the remaining water in the grain. When the bulk of the water is gone, roasting proper starts as the temperature rises towards 374-392 degrees Fahrenheit. The degree of roasting, which is usually monitored by the color development of the beans, plays a major role in determining the flavor characteristics of the final beverage product. Thus, the time and temperature of the roasting are tightly controlled in order to achieve the desired coffee flavor profile. After roasting, the coffee is ground to facilitate extraction during the production of the coffee beverage or coffee extracts (the latter to be used to produce instant coffee products). Again, the type of grinding can influence the final characteristics of the product, such as the flavor of the beverage.

While a considerable amount of research has been carried out on the identification of the flavor molecules in coffee, much less work has been done regarding the physical and chemical reactions that occur within the coffee grains during each of the processing steps. This latter point is particularly evident for the roasting reaction, where the large number of grain constituents undergo an extremely complex series of heat induced reactions (Homma, S. 2001, In "Coffee: Recent Developments". R. J. Clarke and O. G. Vitzthum eds, Blackwell Science, London; Yeretzian, C., et al ((2002) Eur. Food Res. Technol. 214, 92-104; Flament, I (2002) Coffee Flavor Chemistry, John Wiley and Sons, UK; Reineccius, G. A., "The Maillard Reaction and Coffee Flavor" Conference Proceedings of ASIC, 16th Colloque, Kyoto, Japan 1995).

While the details of most of the reactions that occur during the different steps of coffee processing remain relatively unclear, it is understood that the conventional roasting process likely destroys or degrades many beneficial components present in green coffee beans, including phytonutrients such as, for example, Chlorogenic acid. Chlorogenic acids (CGA) are a family of esters formed between certain hydroxycinnamic acids (i.e. caffeic and feluric acids) and (−)-quinic acid. Green (or raw) coffee is a major source of CGA in nature (5-12 g/100 g) (Farah et al. Braz J Plant Physiol. 365 2006; 18:23-36). The major CGA in green coffee are 3-, 4- and 5-caffeoylquinic acids (3-, 4- and 5-CQA), 3,4-, 3,5- and 4,5-dicaffeoylquinic acids (3,4-, 3,5-, and 4,5-diCQA); 3-, 4- and 5-feruloylquinic acids (3-, 4- and 5-FQA) and 3-, 4- and 5-p-coumaroylqunic acids (3-, 4-, and 5-p-CoQA). Caffeoylferuloylquinic acids (CFQA) are minor CGA compounds also found in green coffee, especially in *Coffea robusta* species, as described in U.S. patent application Ser. No. 263292 titled Effects Of A Decaffeinated Green Coffee Extract On Body Weight Control By Regulation Of Glucose Metabolism, filed Oct. 31, 2008 on behalf of Lemaire, et al., and published on May 6, 2010 as publication number U.S. 2010/0112098 A1 (hereafter "Lemaire"), the entirety of which is incorporated herein by reference as though set forth in full herein. Very small amounts of CGA lactones formed by heating during primary processing may also be observed (Farah et al. *Braz J Plant Physiol.* 2006, 18:23-36.—Farah et al. *J Agric Food Chem.* 2005; 53:1505-13).

While green coffee beans have recently been recognized to have some potentially important health benefits (see, e.g., Lemaire, above), products created from green coffee beans have not been widely available like roasted coffee. Part of the reason for this is that processing, preserving and packaging coffee beans in their nutritious, unroasted, "green" state has been difficult, expensive and generally not feasible. For example, Lemaire teaches only extracting certain substances from the green coffee bean, not processing of the entire green coffee bean.

Accordingly, what is needed is an improved method of processing green coffee beans, including partial or whole green coffee beans, that can be used to more easily and inexpensively create green coffee bean products, such as capsules, tablets, mixes, additives, supplements, and the like. Such an improved method is needed to unlock the potential health benefits to consumers of relatively inexpensive products created with green coffee beans, especially whole green coffee beans.

SUMMARY

The present invention addresses these issues and more with novel processing methods for green coffee beans that result in novel green coffee bean products, including products that incorporate whole green coffee beans. Green coffee bean products created and defined by these methods have unexpectedly been found to increase focus and concentration in users, and are believed useful in the treatment of attention deficits. Accordingly, provided herein are novel methods of treatment using green coffee beans and related products comprising whole green coffee beans to increase focus and concentration in users, and to treat attention and concentration deficits and related disorders, such as attention deficit (AD), attention deficit disorder (ADD), attention deficit hyperactivity disorder (ADHD), and various related and/or comorbid disorders.

More specifically, provided in certain embodiments is a method of processing whole green coffee beans to create stabilized whole green coffee bean mixtures, that includes the steps of: selecting whole coffee beans in their fresh green unroasted state with naturally-occurring levels of phytonutrients; sterilizing the coffee beans; reducing the moisture content of the coffee beans; grinding the coffee beans; and mixing at least one stabilizer into the ground coffee beans; wherein all of the aforesaid steps are accomplished without exposing the coffee beans to high enough temperatures for a sufficient amount of time to substantially degrade the naturally-occurring levels of phytonutrients in the coffee beans. In certain embodiments, all of the aforesaid steps are accomplished without exposing the coffee beans to temperatures exceeding about 130 degrees Fahrenheit for more than a few seconds. The whole green coffee beans may comprise *Coffea robusta* coffee beans, and the phytonutrients may include Chlorogenic acid, including in some embodiments at least two percent by weight of Chlorogenic acid. The step of reducing the moisture content of the coffee beans may comprise reducing the moisture content of the coffee beans to less than about two percent. The at least one stabilizer may comprises at least one of, or all of, Magnesium Silicate; Silicon Dioxide; Tricalcium Phosphate.

In various embodiments, the step of grinding the coffee beans may comprise a plurality of iteratively finer grinding steps, such as three increasingly fine steps. For example, the step of grinding the coffee beans may result in most of the ground coffee bean material being sized to pass through a 20 mesh screen.

Also provided are stabilized whole green coffee bean mixtures that necessarily results from and is defined by the foregoing processes. The stabilized whole green coffee bean mixtures may be packaged into at least one of the following forms: packaged in bulk powder form; compressed into a tablet; inserted into a capsule; or mixed with another nutritional supplement or product.

A method is also provided that increases the concentration of and focuses the attention of a user, that includes the step of administering an amount of stabilized whole green coffee bean mixture effective to treat the user.

BRIEF DESCRIPTION OF THE FIGURES

Further features, advantages and characteristics of the present invention will become apparent to a person of ordinary skill in the art in view of the following detailed discussion of example embodiments of the present invention, made with reference to the drawings annexed, in which.

DETAILED DESCRIPTION

Figure 1:
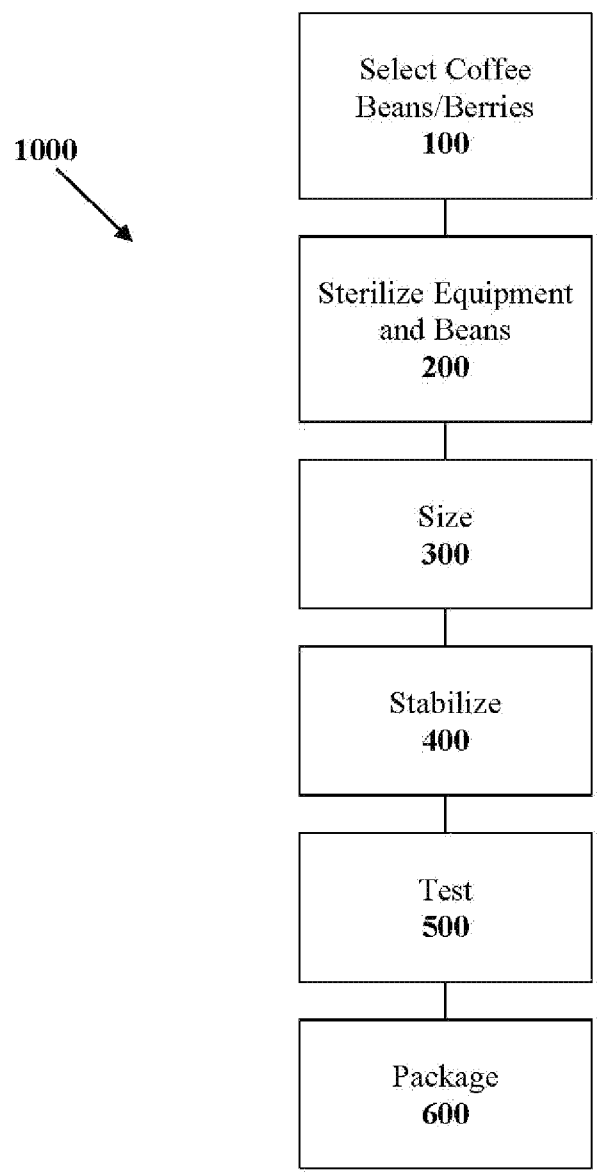
FIG. 1 provides a flow chart showing example steps of a method for processing whole green coffee beans and generating resulting whole green coffee bean products.

FIG. 1 shows a process 1000 for preparing whole or partial green coffee beans for tableting, encapsulation, and or other nutritional uses such as mixes, additives, supplements, and the like. Process 1000 has been developed to tend to preserve the Chlorogenic Acid and other phytonutrient content of the green coffee beans by using relatively low temperatures, for instance in one example not more than about 130 degrees Fahrenheit, throughout the processing steps.

Step 1—Berry Selection:

The first step in process 1000 is berry selection 100. Whole coffee beans are selected in their fresh green unroasted state, preferably with high levels of Chlorogenic Acid and other naturally occurring phytonutrients. For example, the *Coffea robusta* species of berries may be selected. However, any suitable berry or combination of berries may be selected.

Figure 2:
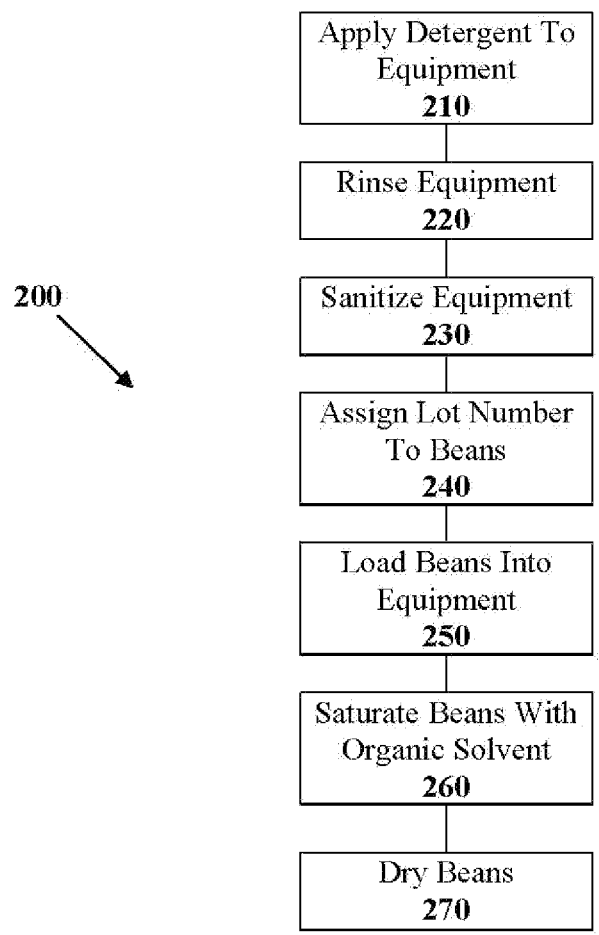
FIG. 2 provides a flow chart showing example sterilization steps of a method for processing whole green coffee beans and generating resulting whole green coffee bean products.

Step 2—Sterilization:

Turning to FIG. 2, in the second step, sterilization 200, the processing machinery must be sterilized. The machinery, such as a ribbon mixer, should be sanitized to make certain that it is clean and free from any debris from products that were processed prior to green coffee. The machinery may also be cleaned with an industrial strength sanitizing solution that kills microbial contamination. In one embodiment, the machinery comprises a Weiler & Company Model 1660 thirty cubic foot ribbon mixer that may be cleaned in a three-step process. In step one, the detergent phase 210, the mixer may be cleaned with trisodium phosphate or similar substance to remove any filth or debris. In step two, clear water rinse 220, the mixer is rinsed thoroughly with clean potable water to remove any detergent residue. Then in step three, the sanitizing phase 230, all food contact surfaces may be saturated with alcohol or other appropriate organic solvent, such as a 70% isopropyl alcohol (IPA) solution, and allowed to air dry.

The whole green coffee beans may have a lot number assigned 240 for the purposes of batch control, for instance in compliance with current Good Manufacturing Practices for Dietary Supplements (cGMP), pursuant to 21 CFR 111. A predetermined amount of the green coffee beans are loaded 250 in the equipment, such as a properly sanitized ribbon mixer. For example, in one embodiment, 100 to 300 kilograms of whole green coffee beans are loaded 250 into a properly sanitized thirty cubic foot ribbon mixer.

The whole green coffee beans are then saturated 260 with an appropriate organic solvent such as IPA. The saturated beans are then dried 270 in a hygienic manner. The saturated beans may be dried by, for instance, removing them from the ribbon mixer and placing them evenly on clean paper-lined trays that are placed in drying racks. The drying Racks may then be moved into a climate controlled drying room set at, for instance, 120-130 degrees Fahrenheit, until they are completely dried. This may take approximately twelve to twenty-four hours, for example to reduce the moisture level of the beans from a typical fifteen percent to less than, for example, two percent.

While example sterilization steps have been provided above, any suitable means of sterilization may be used. A means of sterilization should be suitable if it sufficiently kills yeast, mold, bacteria, and viral contamination that may be present on the beans. This is preferably done for the safety of those consuming the product, and for the purpose of extending the shelf life of the products of which the green coffee beans will become a part. The heating and/or drying aspect 270 of the example process also serves to extend shelf life, as well as to expedite the steps that follow.

Figure 3:
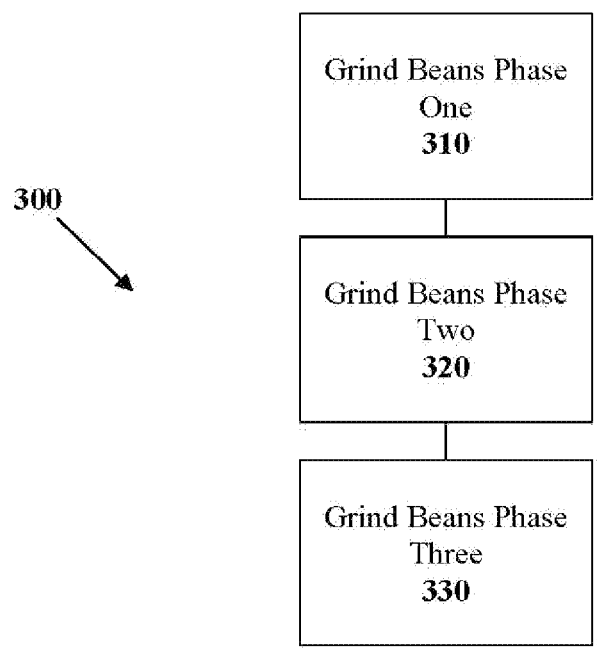
FIG. 3 provides a flow chart showing example sizing steps of a method for processing whole green coffee beans and generating resulting whole green coffee bean products.

Step 3—Sizing:

The third step, sizing 300, an iterative example of which is illustrated in FIG. 3, may be performed using a coffee-grinding mill. Typical coffee-grinding mills tend to generate a great deal of friction and heat. In order to keep the temperature of the beans relatively low during this process, for instance under about 130 degrees Fahrenheit, the whole green coffee beans may be ground down to successively smaller sizes in a plurality of iterative phases. For example, one embodiment employs three iterative phases. In Phase One 310, the sterilized and dried beans are passed through a grinder, such as a Modern Process Equipment 3 HP Coffee Grinder, reducing the size of the bean to, for instance, a minus 8-10 mesh screen size. Then in Phase Two 320, the grinder setting is reduced, for instance from course setting 1 to 3, and the Phase One material is passed through the grinder, further reducing the size so that the material will pass through, for instance, a 12-16 mesh screen. Next, in Phase Three 330, the grinder setting is reduced again, for instance from a course setting 3 to a medium setting in the range of 3 to 7, and the Phase Two material is passed through the mill again until all of the material passes through a smaller screen, such as, for instance, a 20 mesh screen.

Like the other examples provided herein, the above example sizing step 300 is just illustrative of the concept, and the invention is not limited to any of these specific steps unless otherwise stated in the claims. The point is that grinding or milling green coffee is difficult. To preserve its nutritional integrity during the sizing step 300, the green coffee material should not be forced through the mill in a manner that would generate excessive heat, for instance heat that would raise the temperature of the green coffee material above about 130 degrees Fahrenheit. For example, instead of filling or stuffing the grinder with green coffee material and letting it grind, green coffee material can be introduced to the grinder at approximately the same rate as the grinder grinds it on a particular setting.

Note that higher temperatures could be used at various steps and still fall within the scope of the invention, however incremental degradation of the green coffee would likely start to occur according to a time-temperature relationship. For example, the green coffee beans/material may be able to be subject to temperatures exceeding 130 degrees Fahrenheit for several seconds without materially degrading its nutritional components.

Figure 4:
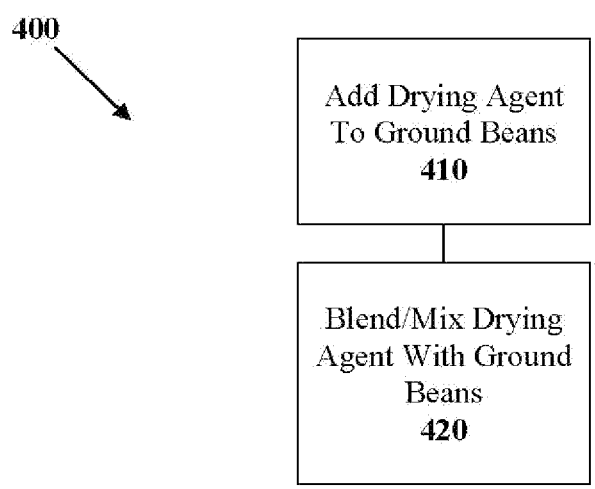
FIG. 4 provides a flow chart showing example steps of a method for stabilizing whole green coffee beans and generating resulting whole green coffee bean products.

Step 4—Stabilization:

Next, the finely ground whole green coffee bean material may be stabilized 400 as illustrated in FIG. 4. During this step 400 the whole green coffee beans that have been ground and classified to predetermined specifications as described above may be placed in a properly sanitized blender. For example, the green coffee bean material may be placed in a Patterson Kelley Twin V sixty-five cubic foot blender that has been sanitized using the three-step process 210, 220, 230 described above. A drying agent may then be introduced 410 to the green coffee bean material. Suitable drying agents may include, for example, Magnesium Silicate, Silicon Dioxide, Tricalcium Phosphate, and the like.

In one example embodiment of the stabilization step 400, six hundred kilograms of sterilized and ground green coffee is placed into a sterilized Patterson Kelley Twin V sixty-five cubic foot blender. Added into the ground green coffee in this example is one to two percent each (by weight) of Magnesium Silicate, Silicon Dioxide, and Tricalcium Phosphate through a 12 mesh screen. That combination may then blended or mixed 420 for ten minutes at twenty-four revolution per minute, creating an example stabilized whole green coffee bean mixture.

While example stabilization steps 410, 420 are described above, any suitable stabilization procedure may be used. Suitable stabilization procedures are those that assist in the long-term preservation of the whole green coffee bean material, as well as the Chlorogenic acid, essential oils and other phytonutrients naturally present in the green coffee beans. Suitable stabilization procedures also typically provide an anti-caking effect that tends to keep the material from clumping when in storage, and tends to provide a free-flowing powder that facilitates the material being tableted, encapsulated, or otherwise used in nutritional products.

Figure 5:
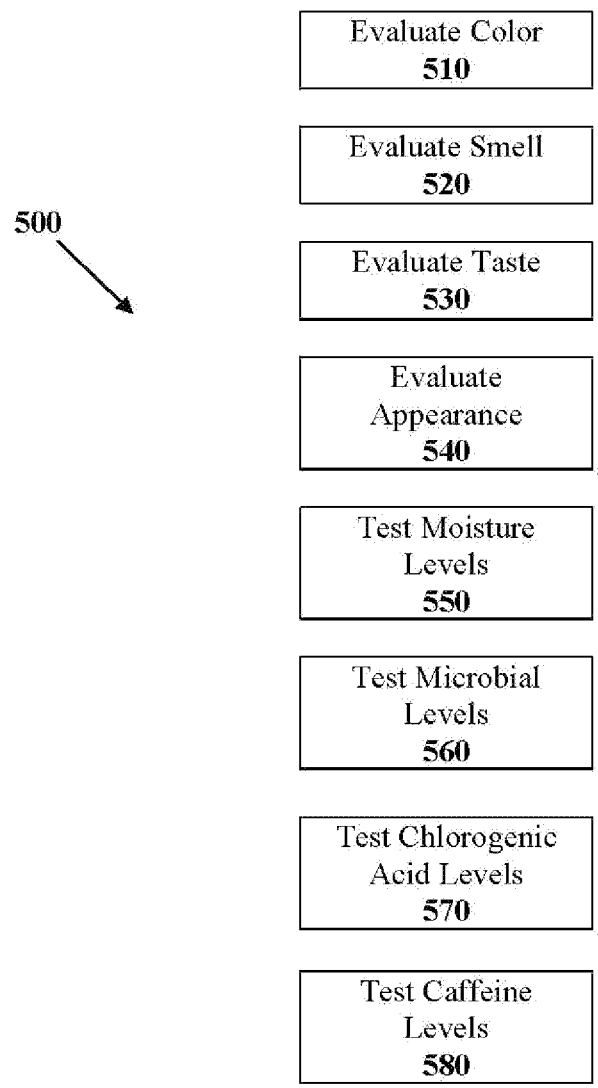
FIG. 5 provides a flow chart showing example steps of a method for testing whole green coffee beans and generating resulting whole green coffee bean products.

Step 5—Testing:

Portions of the stabilized whole green coffee bean mixtures may be tested 500, as shown in FIG. 5. Several parameters may be tested or otherwise evaluated in any appropriate order, including, for example, color 510, odor 520, taste 530, appearance 540, moisture levels 550, microbial levels 560, Chlorogenic acid levels 570, caffeine levels 580, and any other suitable testing, for instance as may be required for various nutritional applications.

For example, color testing 510 may be accomplished by matching the color of the material to a light green laboratory control sample. The material passes if it is the typical color of ground green coffee. The material fails if it is not the typical color of ground green coffee. Similarly, odor or smell testing 520 may be accomplished by, for example, matching the smell of the material to a laboratory control sample. The material passes if it has the typical odor of ground green coffee. The material fails if it does not have the typical odor of ground green coffee. Likewise, taste testing 530 may be accomplished by, for example, matching the taste of the material to a laboratory control sample. The material passes if it has the typical taste of ground green coffee. The material fails if it does not have the typical taste of ground green coffee.

Appearance testing 540 may be accomplished by, for example, passing the material through a 20 mesh screen. The material may be considered to pass if 99% or more passes through the screen.

Moisture level testing 550 may be accomplished by, for example, testing the moisture level of the material. The material may be considered to pass if the moisture level is not more than two percent.

Microbial level testing 560 may be accomplished in various way, including, for example, passing the material if it has a total plate count of not more than 1000, yeast and mold test negative, and coliform tests negative.

Chlorogenic acid level testing 570 may be accomplished using known means.

The material may be considered to pass if, for instance, the Chlorogenic acid levels are not less than two percent.

Caffeine level testing 580 may be accomplished using known means. What levels are considered to pass may change in view of the caffeine level desired in the finished product. Unless otherwise specified, the caffeine level should be the same as naturally occurs in green coffee beans.

The above testing regimens are examples only and are not limiting. Any suitable testing may be performed at any stage of the process 1000.

Figure 6:
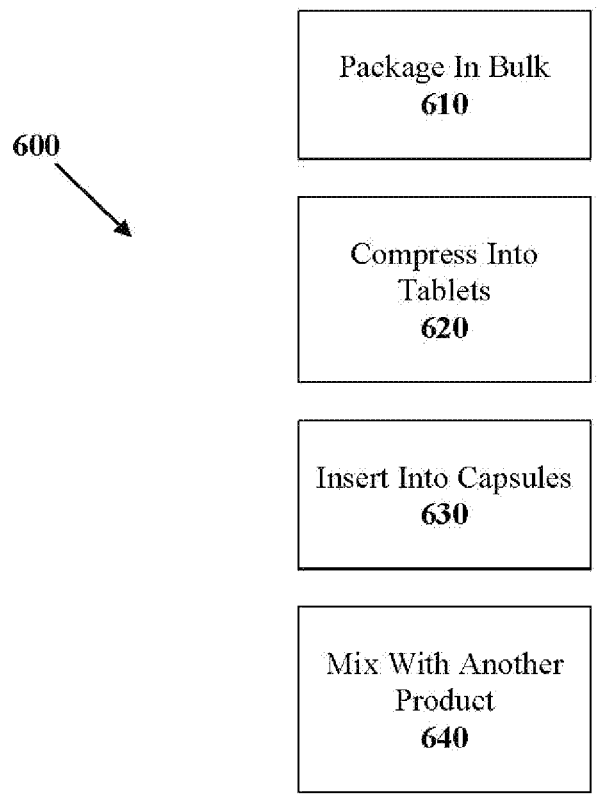
FIG. 6 provides a flow chart showing example steps of a method for packaging whole green coffee beans and generating resulting whole green coffee bean products.

Step 6—Packaging:

The stabilized whole green coffee bean mixtures described above may be packaged 600 in any of numerous ways, some of which are shown in FIG. 6, and many of which are made possible, or at least especially easier, by the foregoing steps. The stabilized whole green coffee bean mixtures may be packaged as oral dosage forms in typical dietary supplement format, added to foods, and/or delivered in a medium for topical, cosmetic use (such as in a cream or ointment, for example). If the stabilized whole green coffee bean mixture is to be consumed directly (as a food additive, for example), it may be flavored, and thereby serve as a dual-purpose product (as a drink-flavoring agent, for example).

For example and not by way of limitation, in certain embodiments the unique and novel stabilized whole green coffee bean mixtures may be packaged 610 in bulk powder form, may be readily compressed 620 into tablets, may be readily inserted 630 into capsules, or may be mixed 640 with another nutritional supplement or product.

Use:

A method of treatment using whole green coffee beans and products comprising whole green coffee beans has unexpectedly been found to dramatically increase focus and concentration in users, and is believed useful in the treatment of attention deficits. Accordingly, provided herein are novel methods of treatment using green coffee beans and related products comprising whole green coffee beans to increase focus and concentration in users, and to treat attention and concentration deficits and related disorders, such as attention deficit (AD), attention deficit disorder (ADD), attention deficit hyperactivity disorder (ADHD), and various related and/or comorbid disorders.

For example and not by way of limitation, the unique and novel stabilized whole green coffee bean mixtures described herein may be administered to a user, for instance orally, to increase the person's focus and concentration. In fact, it has been discovered that certain users may replace their prescription medications for ADD/ADHD with green coffee beans and related products comprising whole green coffee beans. Factors that may be considered in determining suitability and appropriate dosage include the user's age, weight, and other medications the user may be taking, as would be apparent to a person of skill in the art when provided with the present disclosure. For example, it initially appears that users may be able to replace prescription medications for ADD/ADHD with green coffee beans and related products comprising whole green coffee beans, such as, for example, the unique and novel stabilized whole green coffee bean mixtures described herein, unless, for instance, the user is also taking anti-depressants.

In one specific example embodiment, a treatment protocol may comprise a user orally consuming the unique and novel stabilized whole green coffee bean mixtures described herein in the form of tablets, capsules, or any other suitable delivery means, where the dosage contains about fifty-five milligrams of caffeine per dosage. In that example protocol, a user may take one dosage in the morning and one in the afternoon for two consecutive days. If the user has then not yet experienced satisfactory results, the user may continue the treatment with two dosages in the morning and two in the afternoon for two consecutive days. If the user still has then not yet experienced satisfactory results, the user may continue the treatment with three dosages in the morning and three in the afternoon for two consecutive days. It has been found that the above example treatment protocol provides satisfactory results for the vast majority of users. In the rare instances where this protocol is not satisfactory, three dosages may be taken three times a day. It is believed that most users may take three of the above example dosages four times a day without adverse effect.

Using the example dosages provided in the specific embodiment provided above, other example treatment protocols may include: one or two dosages twice a day for persons twelve to sixteen years of age; two dosages in the morning and one dosage in the early afternoon for persons sixteen to eighteen years of age; and two or three dosages in the morning and two dosages in the early afternoon for persons eighteen years of age and older.

All the foregoing dosages and treatment regimens are examples only, and do not limit the scope of the invention except where specifically claimed. Any user, especially those allergic or sensitive to caffeine, should consult with their physician before consuming any of the materials described herein, as with any dietary or energy supplement, and children under the age of eighteen should only consume such products under adult supervision. Products such as those disclosed herein should likely be avoided by those who are or may be pregnant or lactating. Dosages may be self-administered by a user or administered by someone else to a user.

Consuming whole green coffee beans and related products that comprise whole green coffee beans provides unexpected synergistic results compared to traditional coffee products. For example, in the specific examples provided above, three dosages comprise about 165 milligrams of caffeine, which is approximately equivalent to a traditional cup of coffee. But while the primary stimulative effects of a cup of coffee only last about twenty to thirty minutes, consuming three of the example doses described above provides greatly increased concentration and attention that lasts about four to five hours.

Consuming whole green coffee beans as a solid is believed to provide a natural time-release effect, taking about fifteen minutes to begin and lasting for several hours, compared to consuming traditional coffee as a liquid, which causes a rapid up-and-down effect. Consuming products comprising whole green coffee beans, i.e, manufactured from the entire bean, also provides far superior results to consuming chemicals extracted or isolated from coffee beans, such as extracted Chlorogenic acid. Accordingly, the presently disclosed whole green coffee bean products and methods of use provide other unexpectedly superior effects in addition to increased concentration and focus, including but not limited to: improved cardiovascular health; increased resistance to cancer and other diseases; and rapid and sustained weight loss.

The above steps are set forth to illustrate general concepts. Numerous other steps, and combinations and permutations thereof, are contemplated, and are inherently and necessarily disclosed to persons of ordinary skill in the art by the foregoing description.

Although exemplary embodiments and applications of the invention have been described herein, there is no intention that the invention be limited to these exemplary embodiments and applications or to the manner in which the exemplary embodiments and applications operate or are described herein. Indeed, many variations and modifications to the exemplary embodiments are possible as long as the resulting methods and products fall within the scope of one of the following claims or its equivalent.

What is claimed is:

1. A method of processing whole green coffee beans comprising:
    selecting the whole green coffee beans which have been removed from coffee cherries in their fresh green unroasted state with naturally-occurring levels of phytonutrients and having a moisture content;
    sterilizing the unroasted whole green coffee beans;
    reducing the moisture content of the unroasted whole green coffee beans to less than about two percent;
    grinding the unroasted whole green coffee beans to form a material capable of passing through a 20 mesh screen; and
    mixing at least one stabilizer into the material to obtain a stabilized whole green coffee bean mixture;
    wherein all of the aforesaid steps are accomplished without exposing the unroasted whole green coffee beans to temperatures above 130 degrees Fahrenheit for more than several seconds; and
    wherein the sterilizing the unroasted whole green coffee beans comprises saturating the unroasted whole green coffee beans with an organic solvent.

2. The method of claim 1, wherein the whole green coffee beans comprise *Coffea robusta* coffee beans.

3. The method of claim 1, wherein the phytonutrients include chlorogenic acid and wherein the material is not exposed to temperatures above 100 degrees Fahrenheit.

4. The method of claim 3 wherein the organic solvent comprises 70% isopropyl alcohol.

5. The method of claim 3, wherein the at least one stabilizer comprises at least one of: Magnesium Silicate; Silicon Dioxide; Tricalcium Phosphate.

6. The method of claim 5, further comprising a step of packaging the stabilized unroasted whole green coffee bean mixture into a capsule.

7. The method of claim 1, wherein the stabilized whole green coffee bean mixture includes at least two percent by weight of chlorogenic acid.

8. The method of claim 1, wherein the at least one stabilizer comprises at least one of: Magnesium Silicate; Silicon Dioxide; Tricalcium Phosphate.

9. The method of claim 1, wherein the at least one stabilizer comprises all of: Magnesium Silicate; Silicon Dioxide; and Tricalcium Phosphate.

10. The method of claim 1, wherein the step of grinding the unroasted whole green coffee beans comprises a plurality of iteratively finer grinding steps.

11. The method of claim 10, wherein the step of grinding the unroasted whole green coffee beans comprises at least three iteratively finer grinding steps.

12. The method of claim 1, further comprising a step of packaging the stabilized whole green coffee bean mixture into a capsule.

13. The method of claim 1 wherein the organic solvent comprises 70% isopropyl alcohol.

14. A stabilized unroasted whole green coffee bean mixture comprising:
    a material derived from whole green coffee beans which have been removed from coffee cherries, in their fresh green unroasted state with naturally-occurring levels of phytonutrients, by sterilizing the unroasted whole green coffee beans and grinding the whole green coffee beans to a size capable of passing a 20 mesh screen; and
    at least one stabilizer;
    wherein the material has not been exposed to temperatures above 100 degrees Fahrenheit for more than several seconds; and,
    wherein a moisture content of the stabilized unroasted whole green coffee bean mixture is less than about two percent; and
    wherein the sterilizing the unroasted whole green coffee beans comprises saturating the unroasted whole green coffee beans with an organic solvent.

15. The stabilized unroasted whole green coffee bean mixture of claim 14, wherein the whole green coffee beans comprise *Coffea robusta* coffee beans.

16. The stabilized unroasted whole green coffee bean mixture of claim 14 wherein the stabilized whole green coffee bean mixture includes at least two percent by weight of chlorogenic acid and the organic solvent comprises 70% isopropyl alcohol.

17. The stabilized unroasted whole green coffee bean mixture of claim 16, wherein the at least one stabilizer comprises at least one of: Magnesium Silicate; Silicon Dioxide; Tricalcium Phosphate.

18. The stabilized unroasted whole green coffee bean mixture of claim 17, packaged into an orally ingestible capsule or tablet and comprising at least about 55 milligrams of caffeine in the mixture.

19. The stabilized unroasted whole green coffee bean mixture of claim 14 packaged in at least one of the following forms: bulk powder; a tablet; a capsule; a mixture with another nutritional supplement or product.

* * * * *